United States Patent [19]

Meloy

[11] Patent Number: 4,704,911

[45] Date of Patent: Nov. 10, 1987

[54] APPARATUS FOR ANALYSIS OF PARTICULATE MATERIAL

[76] Inventor: Thomas P. Meloy, 5124 Baltan Rd., Bethesda, Md. 20816

[21] Appl. No.: 860,784

[22] Filed: May 8, 1986

[51] Int. Cl.⁴ ............................................. G01N 15/02
[52] U.S. Cl. ................................ 73/865.5; 73/863.24; 73/866; 209/237
[58] Field of Search ................... 73/865.5, 866, 863.24, 73/863.23, 863.25; 209/237, 209, 135

[56] References Cited

U.S. PATENT DOCUMENTS

| | | | |
|---|---|---|---|
| 2,002,974 | 5/1935 | Bennet et al. | 209/237 X |
| 3,203,253 | 8/1965 | Scheid | 73/865.5 |
| 3,795,135 | 3/1974 | Andersen | 73/865.5 X |
| 3,943,754 | 3/1976 | Orr, Jr. | 73/865.5 X |
| 4,161,883 | 7/1979 | Laird et al. | 73/863.24 |
| 4,247,298 | 1/1981 | Rippie | 73/866 X |
| 4,381,669 | 5/1983 | Peters | 73/865.5 |
| 4,382,808 | 5/1983 | Van Wormer, Jr. et al. | 73/863.23 X |

Primary Examiner—Tom Noland
Attorney, Agent, or Firm—Shapiro and Shapiro

[57] ABSTRACT

Apparatus for analysis of particulate material employs a stack of spaced sieves permanently joined to form a sieve column. Clean-out ports are provided for inter-sieve spaces. In one embodiment the clean-out ports communicate with a common passage that is closed by a removable rod. In another embodiment individual clean-out ports are closed by separate plugs. Guard sieves are provided to protect the usual sieves at the ends of the column.

10 Claims, 4 Drawing Figures

U.S. Patent    Nov. 10, 1987    4,704,911
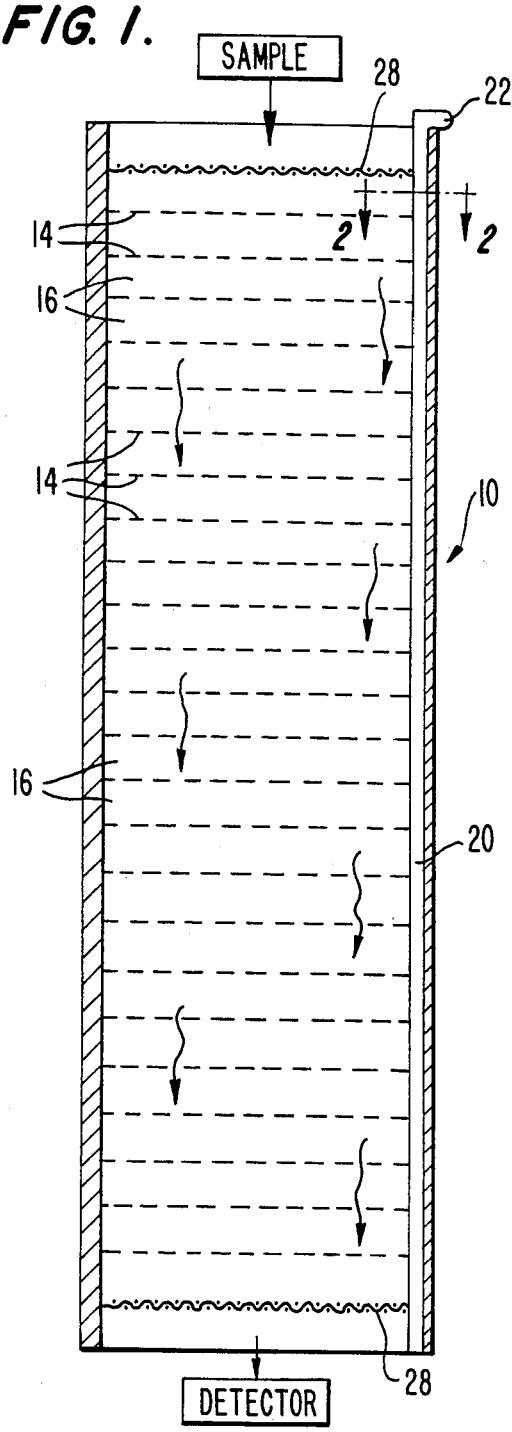
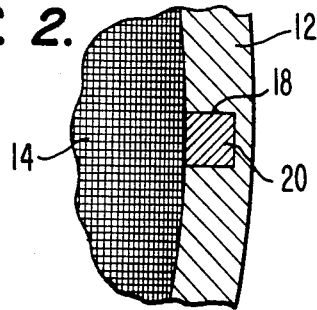
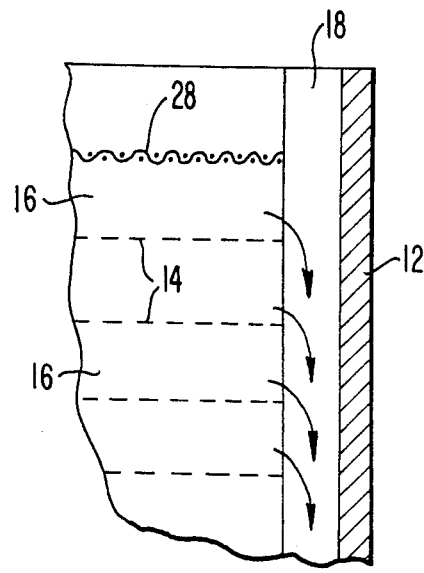
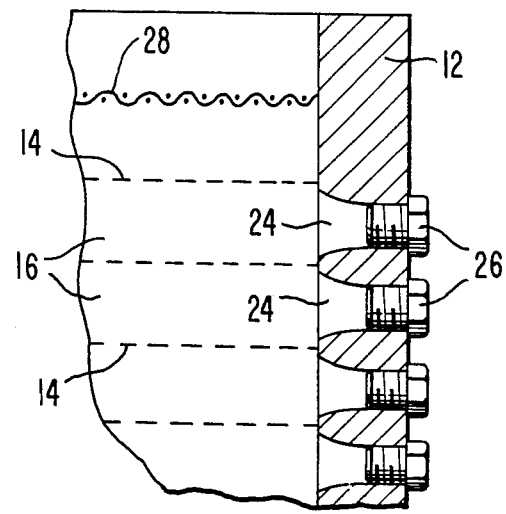

APPARATUS FOR ANALYSIS OF PARTICULATE MATERIAL

BACKGROUND OF THE INVENTION

This invention is concerned with apparatus for analyzing particulate material, such as powders of various types.

My prior U.S. Pat. No. 4,519,244, issued May 28, 1985, and incorporated herein by reference, discloses apparatus and methods for analysis of particulate material by, for example, passing a sample of the material through a series of sieves in a column. Particle characterization is based upon residence time of particles within the column. Particles of different shape, even though their "size" is the same, will pass through a sieve at different rates and will appear at the output of the column at different times, for detection. By virtue of the patented invention, grain, abrasives, and other particulate material can be evaluated with respect to desired qualities. The analysis technique resembles fluid chromatography in certain respects and is referred to as sieve cascadography.

Although ideally the entire sample passes through the sieve column, in practice it has been found that a substantial amount of particulate material may accumulate in the spaces between successive sieves (inter-sieve spaces). In prior sieve cascadographs comprising a series of sieve units stacked and assembled to form the sieve column, the column may be disassembled and the sieves separated to gain access to the inter-sieve spaces for clean-out of accumulated particles. However, the sieves may be formed of fragile material that is easily damaged during cleaning. In any event the assembly and disassembly of the sieves is a laborious procedure.

BRIEF DESCRIPTION OF THE INVENTION

The present invention provides a sieve stack or column in which the sieves may be joined together permanently and yet the inter-sieve spaces easily cleaned out. In addition, sieves at the ends of the stack may be protected by more rugged guard sieves. Although the invention is especially useful in sieve cascadography, it is applicable to other types of apparatus for analysis of particulate material, such as particle size grading apparatus.

In one of its broader aspects, the invention is an apparatus for analysis of particulate material comprising a tubular housing providing therein a flow path for the particulate material between opposite ends of the housing, a stack of spaced sieves in the housing dividing the flow path into a series of inter-sieve spaces that, in use, are isolated from the exterior of the housing except for the flow path, and normally closed clean-out port means for removing particulate material accumulated in the inter-sieve spaces along paths different from the flow path.

The invention will be further described in conjunction with the accompanying drawings, which illustrate preferred (best mode) embodiments.

BRIEF DESCRIPTION OF THE DRAWINGS

FIG. 1 is a somewhat diagrammatic longitudinal sectional view of a first embodiment of the invention;

FIG. 2 is an enlarged fragmentary transverse sectional view taken along line 2—2 of FIG. 1;

FIG. 3. is an enlarged fragmentary longitudinal sectional view illustrating a clean-out operation; and FIG. 4 is a view similar to FIG. 3 of a second embodiment of the invention.

DETAILED DESCRIPTION OF THE INVENTION

As shown in FIG. 1, the invention is applied to a sieve cascadograph 10 comprising a tubular housing 12 containing a plurality of spaced sieves 14. The housing may be a right circular cylinder, for example, and each sieve may be circular also. Typically, there may be 20 sieves in a column 2 to 3 feet tall, although a smaller or larger number of sieves (2 to 1,000, for example) may be employed under appropriate circumstances. The sieve stack or column may be constituted by assembling and permanently joining a series of sieves, each with its own short cylindrical frame. The frames may be stacked and then joined by long rods (not shown), for example, extending through aligned bores in the frames along the length of the column. The exact manner of forming the sieve column is not part of the present invention, but it is preferred that the sieves be joined to one another permanently, rather than removably as in prior sieve cascadographs. The term "sieve" is intended to include not only screens or sieve cloth, but also other members that are permeable to particulate material of different sizes and/or shapes, such as packed beds of spheres, and the like. The interstices of the sieves may be rectangular, round, triangular, or other appropriate shapes.

As shown in FIG. 1, the housing 12 forms a flow path between its upper and lower ends that is divided by the sieves 14 into a plurality of inter-sieve spaces 16. In use of the apparatus 10, the spaces 16 are isolated from the exterior of the housing, except for the flow path. A sample (so designated in FIG. 1) enters the top of the housing, travels along the length of the housing, as indicated by the arrows, and leaves the housing at the bottom for detection by a detector (so designated). Different components of the sample travel through the column of sieves at different rates and leave the column at different times, as explained in my aforesaid patent. Although ideally the entire sample passes entirely through the housing, in practice some of the particulate material accumulates in the inter-sieve spaces. Since many, if not all of the sieves of a sieve cascadograph have the same mesh size, particulate material that accumulates in the inter-sieve spaces cannot be easily removed by merely shaking the apparatus and/or inverting the apparatus. In accordance with the present invention, clean-out ports are provided for the removal of material from the inter-sieve spaces.

As shown in FIG. 3, the housing 12 may have a longitudinal passage 18 extending from one end of the housing to the other through the wall of the housing. In the form shown, the passage is a channel that communicates along one side thereof with the inter-sieve spaces 16 at one side thereof, this communication being indicated in FIG. 3 by the arrows, which designate clean-out paths.

In normal use of the apparatus for analysis, the passage 18 must be closed. For this purpose, a rod 20 is inserted into the passage from one end thereof as shown in FIGS. 1 and 2. In the form shown, rod 20 completely fills the passage 18, blocking any communication between the inter-sieve spaces and the passage, and has an end 22 that engages a corresponding end of the housing to limit the insertion of the rod in the passage 18.

When it is desired to clean out material that has accumulated in the inter-sieve spaces, the rod 20 is withdrawn from the passage 18, and the housing is tilted to cause the accumulated material to enter the passage 18 and to flow through the passage for disposal. If desired, clean-out may be assisted by the application of positive and negative fluid pressure at appropriate points on the apparatus. Also, clean-out of successive inter-sieve spaces can be accomplished in stages, by withdrawing the rod 22 incrementally, when it is desired to observe the material accumulated in each inter-sieve space (as in size grading, for example). This is more easily accomplished in a second embodiment of the invention shown in FIG. 4.

In the apparatus of FIG. 4, each inter-sieve space 16 has an individual clean-out port 24 normally closed by a removable plug 26, that may be threaded into the wall of the housing. The clean-out ports may be wider at their inner ends, as shown, to facilitate the removal of accumulated material when the inter-sieve spaces are tilted toward the clean-out ports.

The sieves of a sieve cascadograph are commonly formed of a rather fragile sieve cloth that is subject to considerable damage from touching, overloading, the application of particles that are too large, or cleaning that is too vigorous. In the preferred form of the invention, where the sieves are permanently fixed in the sieve column, the sieves at the top and bottom of the column are preferably protected by guard sieves 28, as shown in the drawing. The guard sieves are more rugged than the sieves that they are intended to protect and may be formed of stronger sieve cloth or other appropriate material having a multiplicity of openings for the passage of particulate material. A stronger guard sieve above and/or below each sieve at an end of the column (preferably both ends) provides the desired protection and does not interfere with the normal use of the apparatus. The useful life of the apparatus can thus be extended.

While preferred embodiments of the invention have been shown and described, it will be apparent to those skilled in the art that changes can be made in these embodiments without departing from the principles and spirit of the invention, the scope of which is defined in the appended claims.

The invention claimed is:

1. Apparatus for analysis of particulate material comprising a tubular housing providing therein a flow path for the particulate material between opposite ends of the housing, a stack of spaced sieves in said housing dividing said flow path into a series of inter-sieve spaces that, in use, are isolated from the exterior of said housing except for said flow path, and normally closed clean-out port means for removing there-through particulate material accumulated in said inter-sieve spaces along paths different from said flow path.

2. Apparatus in accordance with claim 1, wherein said clean-out port means comprises a passage adapted to communicate with said inter-sieve spaces at one side thereof and having removable means inserted in said passage along the length thereof for normally blocking communication with said inter-sieve spaces.

3. Apparatus in accordance with claim 2, wherein said passage is a channel formed in a wall of said housing and open along one side thereof for communication with said inter-sieve spaces, and wherein said removable means is a rod that fits into said channel from one end thereof.

4. Apparatus in accordance with claim 1, wherein said clean-out port means comprises a passage adapted to interconnect a plurality of said inter-sieve spaces at one side thereof through respective ports having cross-dimensions that are substantially greater than the thickness of the sieves.

5. Apparatus in accordance with claim 1, wherein said clean-out port means comprises a plurality of clean-out ports extending from inter-sieve spaces through a wall of said housing, said ports having cross-dimensions that are substantially greater than the thickness of said sieves and having removable plugs for closing the ports.

6. Apparatus in accordance with claim 1, wherein said apparatus is a sieve cascadograph and wherein a plurality of said sieves have substantially the same mesh size.

7. Apparatus in accordance with claim 1, wherein at least one of said sieves adjacent to an end of said flow path that is open to the exterior of said housing is composed of a fragile material and has guard means at the exterior thereof, said guard means being composed of a material stronger than the fragile material and providing a multiplicity of openings therethrough for the passage of said particulate material to or from said housing.

8. Apparatus in accordance with claim 7, wherein said sieves are permanently mounted in said housing and said guard means is provided at both ends of the housing.

9. Apparatus for analyzing particulate material, comprising a tubular housing providing a flow path between opposite ends of the housing, a plurality of spaced sieves in said housing dividing said flow path into a series of inter-sieve spaces, at least one of the sieves adjacent to an end of said flow path that is open to the exterior of said housing being composed of fragile material and having guard means at the exterior thereof, said guard means being composed of a material stronger than the fragile material and providing a multiplicity of openings therethrough for the passage of said particulate material to or from said housing.

10. Apparatus in accordance with claim 9, wherein said sieves are permanently mounted in said housing and said guard mean is provided at both ends of the housing.

* * * * *